United States Patent [19]

Jamerson et al.

[11] 4,446,074
[45] May 1, 1984

[54] PREPARATION OF RHODIUM COMPLEX COMPOUNDS

[75] Inventors: Jackie D. Jamerson; Ernst Billig, both of Charleston; David R. Bryant, South Charleston, all of W. Va.

[73] Assignee: Union Carbide Corporation, Danbury, Conn.

[21] Appl. No.: 334,198

[22] Filed: Dec. 24, 1981

[51] Int. Cl.$^3$ .............................................. C07F 15/00
[52] U.S. Cl. ................................. 260/429 R; 502/20; 502/166
[58] Field of Search ................ 260/429 R; 252/431 P, 252/411 R

[56] References Cited

U.S. PATENT DOCUMENTS

| | | | |
|---|---|---|---|
| 3,527,809 | 9/1970 | Pruett et al. | 252/431 R X |
| 3,547,964 | 12/1970 | Olivier | 260/429 R |
| 3,560,539 | 2/1971 | Booth | 260/429 R |
| 3,641,076 | 2/1972 | Booth | 260/429 R |
| 3,644,446 | 2/1972 | Booth et al. | 260/429 R |
| 3,755,393 | 8/1973 | Kniese et al. | 260/429 R |
| 3,857,895 | 12/1974 | Booth | |
| 3,859,359 | 1/1975 | Keblys | 260/429 R X |
| 3,965,192 | 6/1976 | Booth | 260/429 R |
| 4,021,463 | 5/1977 | Kummer et al. | 260/429 R |
| 4,113,754 | 9/1978 | Kummer et al. | 260/429 R |
| 4,201,714 | 5/1980 | Hughes | 260/429 R X |
| 4,221,743 | 9/1980 | Halstead et al. | 252/431 P X |
| 4,277,414 | 7/1981 | Saito et al. | 260/429 R |
| 4,297,239 | 10/1981 | Bryant et al. | 252/411 R X |
| 4,363,764 | 12/1982 | Billig et al. | 260/429 R |

OTHER PUBLICATIONS

Evans, et al., J. Chem. Soc. (A), pp. 2660–2665, (1968).
Gregorio, et al., Inorg. Chem. Acta. vol. 3, No. 1, pp. 89–93, (1969).
Ahmad, et al., Inorganic Synthesis, vol. XV, Chapt. 3, pp. 45 to 47 & 59 to 60, (1974).

Primary Examiner—Helen M. S. Sneed
Attorney, Agent, or Firm—R. S. Finnegan

[57] ABSTRACT

Process for preparing hydridocarbonyltris(triorganophosphorus) rhodium compounds.

15 Claims, No Drawings

PREPARATION OF RHODIUM COMPLEX COMPOUNDS

BACKGROUND OF THE INVENTION

This invention relates to a process for preparing hydridocarbonyltris(triorganophosphorus) rhodium compounds. More particularly this invention relates to an organic one-phase process for preparing hydridocarbonyltris(triorganophosphorus) rhodium compounds directly from an organic concentrate of a spent hydroformylation reaction medium.

Various methods for preparing hydridocarbonyltris(triorganophosphorus) rhodium compounds are well known in the art as seen for example by U.S. Pat. Nos. 3,560,539; 3,644,446; 3,965,192; 4,021,463 and 4,113,754 as well as applicants' U.S. application Ser. No. 221,502 filed Dec. 30, 1980, now U.S. Pat. No. 4,363,764. However, said references are in general directed to aqueous phase type transfer processes or processes that involve the hydrogenation of a halocarbonylbis(triorganophosphine) rhodium compound in the presence of triorganophosphorus ligand to produce the desired hydridocarbonyltris(triorganophosphorus) rhodium complex. Moreover, heretofore in those instances where the hydridocarbonyltris(triorganophosphorus) rhodium complex is produced from non-halogenated rhodium compounds the rhodium starting materials are relatively simple rhodium compounds in contrast to the recovered rhodium starting materials employed in the process of this invention as explained more fully below.

SUMMARY OF THE INVENTION

It has now been discovered that hydridocarbonyltris(triorganophosphorus) rhodium compounds can be prepared by an organic one-phase process that is especially suitable for recovering the spent rhodium values of large scale commercial hydroformylation operations by converting the spent rhodium of such operations into high yields of said hydridocarbonyltris(triorganophosphorus) rhodium compounds.

Thus it is an object of this invention to provide an organic one-phase process for preparing said hydridocarbonyltris(triorganophosphorus) rhodium compounds directly from an organic concentrate of a spent hydroformylation reaction medium. Other objects and advantages of this invention will become readily apparent from the following written description and appended claims.

Accordingly a generic aspect of this invention can be described as an organic one-phase process for preparing a hydridocarbonyltris(triorganophosphorus) rhodium compound which comprises reacting, at a temperature from about 20° C. to about 120° C., an essentially non-aqueous, homogeneous organic reaction solution consisting essentially of (a) a rhodium complex concentrate, (b) hydrogen gas or a hydrogen source, (c) an alcoholic diluent (d) carbon monoxide gas or a carbon monoxide source, and (e) free triorganophosphorus ligand, for at least a sufficient period of time to form said hydridocarbonyltris(triorganophosphorus) rhodium compound; said rhodium complex concentrate consisting essentially of from about 0.1 to about 30 percent by weight of a spent hydroformylation reaction medium and having been produced by concentrating a spent hydroformylation reaction medium that contains a partially deactivated soluble rhodium complex hydroformylation catalyst, aldehyde products, higher boiling aldehyde condensation by-products and free triorganophosphorus ligand, so as to remove from said medium, while retaining a major amount of the rhodium values of said catalyst present in said medium, at least essentially all of said aldehyde products, at least 50 percent by weight of said higher boiling aldehyde condensation by-products that have a boiling point below that of said free triorganophosphorus ligand present in said medium and at least 50 percent by weight of said free triorganophosphorus ligand present in said medium.

DESCRIPTION OF THE PREFERRED EMBODIMENTS

As seen discussed above one of the points of novelty of this invention rests in the discovery that a rhodium complex concentrate of a spent hydroformylation reaction medium can be employed as the starting material of this invention. Such rhodium complex concentrates consist essentially of from 0.1 to about 30 percent by weight of a spent hydroformylation reaction medium and are produced by concentrating said medium to said desired rhodium complex concentrate. More preferably the rhodium complex concentrate consists essentially of from about 1 to about 10 percent by weight, and most preferably from about 2 to about 6 percent by weight of the spent hydroformylation reaction medium.

The term "spent hydroformylation reaction medium" as employed herein means any hydroformylation reaction medium, or any part thereof, containing a rhodium complex hydroformylation catalyst, aldehyde products, higher boiling aldehyde condensation by-products and free triorganophosphorus ligand that has been employed in any process directed to producing aldehydes by hydroformylating an olefinic compound with carbon monoxide and hydrogen and which process has been operated to the extent that said catalyst has become at least partially deactivated. Thus the particular hydroformylation process and reaction conditions for producing aldehydes from which the spent hydroformylation reaction medium is derived are not narrowly critical features of the present invention, since such serves only as a means of supplying the spent hydroformylation reaction medium to be concentrated to the rhodium complex concentrate starting material of this invention. Thus while the spent hydroformylation mediums concentrated according to this invention may be derived from any suitable hydroformylation process, such as disclosed e.g. in U.S. Pat. No. 3,527,809 and the article "Industrialization of Rhodium Process Oxo Reaction Technology" by Yamaguchi in *Niddakyo Gepto.* Vol. 32, No. 3, pp. 14–22 (1979), the preferred spent hydroformylation reaction mediums are derived friom continuous hydroformylation procedures such as taught e.g. in U.S. Pat. Nos. 4,148,830 and 4,247,486 and U.S. application Ser. No. 190,280 filed Sept. 24, 1980, the disclosures of which are incorporated herein by reference thereto. Moreover, in general it is preferred to concentrate those spent hydroformylation reaction mediums in which the rhodium complex catalyst has become at least 60 percent deactivated and more preferably that has become so deactivated that it is no longer economical to continue the hydroformylation process. However, it is not necessary to await such an event, since the rhodium complex concentrate of this invention can be derived from any such spent hydroformylation reaction medium which contains at least a partially deactivated rhodium hydroformylation catalyst, i.e. a catalyst which is less active than its original counterpart. The extent of deactivation of the catalyst may be determined at any given time during the hydroformylation reaction, e.g. by comparing the conversion rate to product based on such catalyst to the conversion rate obtained using fresh catalyst.

Thus the spent hydroformylation reaction mediums employable in this invention are those that contain a partially deactivated rhodium complex catalyst, aldehyde products, higher boiling aldehyde condensation by-products and free triorganophosphorus ligand and can contain additional ingredients which have either been deliberately added to the reaction medium of the hydroformylation process or formed in situ during said process.

Accordingly the partially deactivated rhodium complex hydroformylation catalyst, present in the spent hydroformylation reaction medium to be concentrated according to this invention can be any rhodium hydroformylation catalyst suitable for use in a hydroformylation reaction and which has been employed in a hydroformylation reaction to the extent that it has become partially deactivated i.e. does not have the same rate of activity of corresponding fresh rhodium complex catalyst.

Thus the particular partially deactivated rhodium complex hydroformylation catalyst, as well as its amount, present in a given spent hydroformylation reaction medium to be concentrated will obviously correspond to and merely be dependent upon the particular rhodium complex hydroformylation catalyst employed in and/or formed under the reaction conditions of the hydroformylation reaction from whence the spent hydroformylation reaction medium to be concentrated has been derived. In general such rhodium complex hydroformylation catalysts comprise rhodium complexed with a triorganophosphorus ligand. For example, as seen by the preferred operational features taught in U.S. Pat. Nos. 3,527,809, 4,148,830 and 4,247,486, the preferred hydroformylation reaction mediums contain a rhodium complex catalyst consisting essentially of rhodium complexed with carbon monoxide and triarylphosphine (corresponding to the free triarylphosphine ligand also contained in said medium). As such hydroformylation reactions continue, alkyl substituted phosphine is formed in situ, the amount of which continues to build up over the period of time that a continuous hydroformylation reaction is operational. Said alkyl substituted phosphine ligand having a greater affinity for rhodium than triarylphosphine may also tie or bind itself to the rhodium thereby resulting in a rhodium complexed catalyst consisting essentially of rhodium complexed with carbon monoxide, triarylphosphine ligand and/or said alkyl substituted phosphine ligand (i.e. either one or both of said triarylphosphine ligand and said alkyl substituted phosphine ligand). Thus, it is to be understood that the rhodium complex catalyst terminology "consisting essentially of", as employed herein, is not meant to exclude, but rather include the likely possibility of alkyl substituted phosphine and hydrogen complexed with the rhodium in addition to carbon monoxide and triarylphosphine, the hydrogen being derived from the hydrogen gas of the hydroformylation reaction if not already present in the catalyst precursor.

As pointed out in the above discussed prior art the rhodium complex hydroformylation complex catalyst may be formed in situ during the hydroformylation reaction or preformed by methods known in the art. Thus it is not intended to limit the present invention by any explanation as to the exact nature of the active rhodium complex hydroformylation catalyst or to the nature of the deactivated rhodium hydroformylation catalyst formed during the hydroformylation reaction. Clearly it is sufficient for the purpose of this invention to simply point out that carbon monoxide, triorganophosphorus compounds and hydrogen are all ligands that are capable of being complexed with the rhodium to form both the active and/or partially deactivated rhodium complex catalyst of a hyroformylation reaction.

Accordingly, in general the amount of partially deactivated rhodium complex hydroformylation catalyst present in the spent hydroformylation reaction medium to be concentrated according to this invention will correspond to that catalytic amount of rhodium catalyst present in the hydroformylation reaction from whence said medium to be concentrated has been derived, and may be that amount sufficient to provide a rhodium concentration in said medium to be concentrated which may range from about 25 ppm to about 1200 ppm and preferably from about 50 ppm to about 600 ppm of rhodium calculated as free metal.

The particular aldehyde products present in a given spent hydroformylation reaction medium to be concentrated according to this invention will obviously correspond to those aldehyde products produced by the particular hydroformylation reaction from whence the spent hydroformylation reaction medium to be concentrated has been derived. Preferably such aldehyde products are mixtures rich in their normal isomers, i.e., contain at least about four moles of normal aldehyde product per mole of isomeric aldehyde product. For example, the continuous hydroformylation of propylene produces butyraldehyde products, which products under preferred operational conditions are rich in normal butyraldehyde. Of course, the particular aldehyde products contained in a given spent hydroformylation reaction medium to be concentrated will also depend upon the particular olefinic compound employed in the hydroformylation reaction from whence said medium to be concentrated is derived. Said aldehyde products, of course, each contain one more carbon atom than the olefinic compound employed in the hydroformylation reaction. Olefinic compounds that may be employed in such hydroformylation reactions include those containing from 2 to 20 carbon atoms and which may contain groups or substituents that do no essentially interfere with the course of the hydroformylation reaction and the process of this invention, such as generically taught in the prior art, especially U.S. Pat. No. 3,527,809. Illustrative olefinic compounds include alkenes such as alpha olefins and internal olefins, alkyl alkenoates, alkenyl alkanoates, alkenyl alkylethers, alkenols and the like. The preferred olefinic compounds are alpha-olefins containing from 2 to 20 carbon atoms and more preferably from 2 to 6 carbon atoms, such as ethylene, propylene, 1-butylene, 1-pentylene, 1-hexylene, and the like.

Thus the spent hydroformylation reaction medium to be concentrated according to this invention will also contain at least some portion of the aldehyde products produced by the particular hydroformylation reaction involved from whence said spent mediums are derived. In general the amount of aldehyde products present in the spent hydroformylation reaction medium to be concentrated according to this invention may range from about 1.0 to about 80 percent by weight and more preferably from about 10 to about 60 percent by weight, based on the total weight of said spent hydroformylation reaction medium to be concentrated.

As is known in the prior art, during such hydroformylation reactions a substantial amount of higher boiling aldehyde condensation by-products is formed in situ and is preferably retained in the hydroformylation reaction medium of the reaction to serve as a solvent for the rhodium complex hydroformylation catalyst as fully explained in said U.S. Pat. Nos. 4,148,830 and 4,247,486. Moreover, in general the major amount of such higher boiling aldehyde condensation by-products are liquid condensation by-products having a boiling point below that of the free triorganophosphorus ligand present in the hydroformylation reaction medium, while a minor amount of such higher boiling aldehyde condensation by-products are those liquid condensation by-products having a boiling point above that of the free triorganophosphorus ligand present in the hydroformylation reaction medium. For example, in the continuous hydroformylation of propylene to produce butyraldehyde in the presence of free triphenylphosphine ligand the higher boiling aldehyde condensation by-products generally comprise a major amount of various trimer and tetramer aldehyde condensation by-products that have a boiling point below that of said free triphenylphosphine ligand a minor amount of pentamer aldehyde condensation by-products and the like that have a boiling point above that of said free triphenylphosphine ligand. Thus it is to be understood that the term "higher boiling aldehyde condensation by-products" as employed herein, unless otherwise specifically designated, includes mixtures of both such types of by-products, i.e. those having a boiling point below that of the free triorganophosphorus ligand present in the hydroformylation reaction medium and those having a boiling point above that of the free triorganophosphorus ligand present in the hydroformylation reaction medium. Accordingly the particular higher boiling aldehyde condensation by-products, as well as their total amount, present in a given spent hydroformylation reaction medium to be concentrated according to this invention will generally correspond to those higher boiling aldehyde condensation by-products retained in the hydroformylation reaction medium and formed in situ during the particular hydroformylation reaction from whence the spent hydroformylation reaction medium to be concentrated has been derived. In general the total amount of higher boiling aldehyde condensation by-products present in the hydroformylation medium to be concentrated according to this invention may range from about 5 to about 95 percent by weight and more preferably ranges from about 50 to about 90 percent by weight, based on the total weight of said medium to be concentrated.

The free triorganophosphorus ligand i.e. that amount of triorganophosphorus ligand that is not complexed with or tied to the rhodium complex hydroformylation reaction catalyst as well as the triorganophosphorus ligand complexed with the rhodium complex hydroformylation catalyst present in the spent hydroformylation reaction medium to be concentrated according to this invention will obviously correspond to those particular phosphorus ligands employed in the particular hydroformylation reaction from whence the spent hydroformylation reaction medium to be concentrated has been derived and thus can be any triorganophosphorus ligand suitable for such hydroformylation reaction technology. Such triorganophosphorus ligands are well known in the art as seen by the above discussed references, the more common ligands being triorganophosphites and triorganophosphines. Triorganophosphine ligands are presently preferred, especially triarylphosphines, the most preferred ligand being triphenylphosphine. In general the amount of free triorganophosphorus ligand present in the spent hydroformylation reaction medium to be concentrated according to this invention may range from about 1 percent by weight to about 25 percent by weight and more preferably from about 5 percent by weight to about 20 percent by weight, based on the total weight of said medium to be concentrated. Moreover, in preferred continuous hydroformylation reactions particularly advantageous results are achieved when the amount of free triorganphosorus ligand in the hydroformylation reaction medium of such reactions is at least about 100 moles of free triorganophosphorus ligand per mole of catalytically active rhodium metal present in the rhodium complex hydroformylation catalyst. Thus the preferred hydroformylation reaction medium to be concentrated according to this invention will also generally contain at least about 100 moles of free triorganophosphorus ligand per mole of catalytically active rhodium metal present in the rhodium complex hydroformylation catalyst of said medium to be concentrated.

Moreover such spent hydroformylation mediums to be concentrated may also contain in conventional amounts, additional ingredients deliberately added to or formed in situ during the hydroformylation process from whence said spent mediums are derived. For example, such hydroformylation processes may be conducted in the present of any additional suitable organic solvent, e.g., such as disclosed and described in U.S. Pat. No. 3,527,809. Further such spent hydroformylation reaction mediums may contain other triorganophosphorus ligands that are different from the main free triorganophosphorus ligand present in the reaction medium of the hydroformylation process as a result of deliberate addition or in situ formation. For instance, U.S. Pat. No. 4,260,828, the entire disclosure of which is incorporated herein by reference thereto, discloses that the stability of the rhodium complex catalyst can be enhanced by the presence of an alkyldiarylphosphine which may be deliberately added to the reaction medium of the hydroformylation process or formed in situ. For example the continuous hydroformylation of propylene in the presence of free triphenylphosphine ligand results in the in situ production of propyldiphenylphosphine. Likewise such spent hydroformylation reaction mediums may also obviously contain some unreacted olefinic starting materials and in addition may further contain organophosphorus oxides which correspond to the organophosphorus ligands present in the reaction medium of the hydroformylation process, which oxides may be the result of in situ formation during the process due to adventitious oxygen or as the result of a deliberate oxidative treatment of the reaction medium of the process, e.g. as disclosed in U.S. Pat. No. 4,221,843 and said Ser. No. 190,280.

The rhodium complex concentrate employable in this invention can be produced by any conventional method or combination of methods which comprises forming a rhodium complex concentrate consisting essentially of from about 0.1 to about 30 percent by weight by concentrating a spent hydroformylation reaction medium as defined above so as to remove, while retaining a major amount of the rhodium values of the partially deactivated rhodium complex catalyst present in said medium, at least essentially all of the aldehyde products present in said medium, at least 50 percent by weight of the higher boiling aldehyde condensation by-products present in said medium that have a boiling point below that of the free triorganophosphorus ligand present in said medium, and at least 50 percent by weight of the free triorganophosphorus ligand present in said medium.

For example, it is generally preferred to concentrate the spent hydroformylation reaction medium by means of distillation as taught in U.S. Pat. No. 4,297,239, the entire disclosure of which is incorporated herein by reference thereto. Such a procedure involves concentrating the spent hydroformylation reaction medium into at least two material streams by means of distillation at temperatures of about 20° to about 350° C. and at pressures of about 1000 to about $1 \times 10^{-6}$ mm. Hg., wherein one stream is said rhodium complex concentrate (i.e. the distillation residue) containing a major amount of the rhodium values of the partially deactivated rhodium hydroformylation catalyst present in said medium and which has been concentrated to about 0.1 to about 0.1 to about 30 percent by weight of said spent hydroformylation reaction medium, and the other material stream or streams consist essentially of one or more of the distilled volatiles of said spent hydroformylation reaction medium, i.e. the aldehyde products, higher boiling aldehyde condensation by-products having a boiling point below that of the free triorganophosphorus ligand present in said medium, and the free triorganophosphorus ligand of said medium.

The distillation procedure preferably takes place in two stages, the first stage being conducted at temperatures of about 20° to 250° C., preferably from 20° to 190° C., and pressures of about 1000 to about 0.1 mm Hg., preferably about 150 to 0.5 mm Hg., which may effect up to about a threefold concentration of the spent hydroformylation reaction medium; the second stage of the distillation being conducted at temperatures of about 25° to 350° C., preferably from about 150° to about 300° C., and pressures of about 100 to $1 \times 10^{-6}$ mm Hg., preferably about 20 to 0.1 mm Hg., so as to further concentrate the bottom or residue product of the first stage to the finally desired rhodium complex concentrate which may contain from about 1000 to about 70,000 ppm, more preferably from about 1500 to about 15,000 ppm, and most preferably from about 2,000 to 12,000 ppm, of rhodium calculated as free metal.

The first distillation stage is employed to distill off and remove the most volatile components, e.g. the aldehyde products, that are present in the spent hydroformylation medium since such low boiling volatile components interfere with obtaining the desired low pressures employed in the second distillation stage and needed for the most effective removal of the less volatile (i.e. higher boiling) components and said free triorganophosphorus ligand present in said medium.

The second distillation stage involves taking the liquid residue or bottoms of said first distillation stage containing the partially deactivated rhodium complex catalyst and less volatile components, such as said higher boiling aldehyde condensation by-products and the free triorganophosphorus ligands of the spent hydroformylation reaction medium, and subjecting it to further distillation at the reduced pressures given above so as to distill off and remove free triorganophosphorus ligand and the higher boiling aldehyde condensation by-products that have a boiling point above said aldehyde products but below that of the free triorganophosphorus ligand present in said residue. The desired rhodium complex concentrate employable in this invention is thus recovered as the distillation residue of said second stage distillation and contains a major amount of the rhodium values of said partially deactivated catalyst (i.e. more than 50 percent by weight, preferably more than 90 percent by weight, of the total amount of rhodium values of said catalyst). For obvious economic reasons it is most desirable that the rhodium complex concentrate contain essentially (i.e. greater than 97 percent by weight) all of the rhodium values of said partially deactivated catalyst.

The distillation of each separation stage can be carried out by using any suitable distillation system and can take place on a continuous and/or discontinuous (batch) basis. However, care should be taken to avoid overheating the rhodium complex. It is also important to maintain a high vacuum in the second distillation stage so that the temperature required for concentration can be minimized. Thus the distillation is preferably carried out at the lowest temperature and shortest residence time required to achieve the desired rhodium concentration. Accordingly it is preferred to employ a thin-film evaporator, such as a wiped-film evaporator, since in such systems residence times at elevated temperatures of less than 10 minutes should be suitable in most instances, and preferably such residence times will be less than about three minutes, whereas in a kettle-type batch distillation the residence time for the second stage of distillation can be hours. However, batch systems are readily suitable for the first stage of distillation, since such is concerned with only removing the most volatile (lower boiling) components of the spent medium and thus the distillation can be carried out at rather mild temperatures and at much higher pressures than those pressures employed in the second distillation stage. In general, it is preferred to carry out both distillation stages in a thin-film evaporator, especially a wiped-film evaporator. Such evaporators are well known in the art and thus need not be further discussed herein. Of course, it is also to be understood that the procedure of each distillation stage can be carried out more than once, i.e., repeated until the desired amount of volatiles have been removed and/or the desired rhodium concentration obtained.

It should be noted that a fundamental change in the rhodium species present in the partially deactivated catalyst occurs during the distillation concentration procedure. The rhodium species found in the rhodium complex concentrates produced by the distillation concentration procedure are different in that it is generally larger in size than those species found in partially deactivated rhodium complex catalysts. Said rhodium complex concentrates so obtained have a dark brownish color and are highly viscous rhodium complex mediums.

Moreover, adding an oxidant such as oxygen and/or an organic peroxide to the rhodium complex concentrates employable in this invention can lead to an increase in the yield of desired hydridocarbonyltris(triorganophosphorus) rhodium compound prepared according to this invention.

It is difficult to ascertain the precise reasons for such an improvement in the yield of the hydridocarbonyltris(triorganophosphorus) rhodium compound produced according to this invention when the rhodium complex concentrate is contacted with an oxidant. However, it is believed that the oxidant, for whatever reason, somehow renders the large rhodium clusters obtained in preparing the concentrates which are a dark brown liquid more susceptible to reaction with the hydrogen, carbon monoxide and triorganophosphorus ligand employed in forming the desired hydridocarbonyltris(triorganophosphorus) rhodium complex compound.

The oxidant employed for treatment of the rhodium complex concentrate may be in the form of a gas or liquid and may be selected from the class consisting of oxygen and an organic peroxide, that is to say that the oxidant can be oxygen and/or an organic peroxide. While the preferred oxidant is oxygen it is to be understood that oxygen need not be employed in its pure form, but more preferably and conveniently is employed in the form of or in admixture with an inert gas, such as nitrogen in order to minimize any explosive hazards. Indeed while oxygen in the form of air is the most preferred and convenient oxidant it too may be diluted with an inert gas such as nitrogen in order to reduce its oxygen content if operating conditions warrant such safety precautions. The liquid organic peroxides which may also be employed as oxidants herein encompass organic peroxides of the formula R—O—O—R', wherein R represents a radical selected from the group consisting of monovalent hydrocarbon radicals of 2 to 20 carbon atoms, aroyl radicals of 7 to 20 carbon atoms, alkoxycarbonyl radicals of 2 to 20 carbon atoms and cycloalkoxycarbonyl radicals of 4 to 20 carbon atoms, and wherein R' represents a radical selected from the group consisting of hydrogen and a radical represented by R as defined above. Preferred monovalent hydrocarbon radicals represented by R and R' above are alkyl and aralkyl radicals, especially t-alkyl radicals of 4 to 20 carbon atoms and aralkyl radicals of 8 to 15 carbon atoms. Most preferably R' represents hydrogen (i.e. —H). Illustrative organic peroxides include t-butylhydroperoxide, t-amylhydroperoxide, cumenehydroperoxide, ethylbenzenehydroperoxide, and the like. Such organic peroxides and/or methods for their preparation are well known in the art, the most preferred organic peroxide being t-butylhydroperoxide.

Further it is to be appreciated that the improvement in the yield of desired hydridocarbonyltris(triorganophosphorus) rhodium compound due to the rhodium complex concentrate's treatment with the oxidant may be accomplished by adding the oxidant to the concentrate in any manner which seems most convenient and suitable. Thus the method of treating the concentrate with the oxidant is not critical and can be accomplished simply by adding a sufficient amount of oxidant to the concentrate to obtain the desired improvement in the yield of hydridocarbonyltris(triorganophosphorus) rhodium compound. For instance, the gaseous or liquid oxidant can be added by carrying out the concentration of the spent hydroformylation medium in the presence of the oxidant, or during or after the concentrate is being collected. By way of example the liquid organic peroxides may be added to spent hydroformylation medium prior to the concentration procedure or to the concentrate while or after it is being collected. Likewise oxygen, and more preferably air, can be sparged into the concentrate after it has been collected, as it is being collected or while it is still a film on the walls in the thin film evaporator. The concentrate can also be agitated or stirred so as to create a vortex that will draw air from overhead into said concentrate. Alternatively spraying or atomizing the concentrate into air or allowing air to diffuse into the concentrate while or after concentration may also be employed. However because oxygen is the more preferred oxidant and because diffusion of air into the viscous concentrate can be quite slow, in order to obtain the most optimum results it is generally preferred to thoroughly disperse air throughout the concentrate, such as e.g. by directly feeding air into the concentrate after it has been collected or while it is still a film on the walls in a thin film evaporator or by agitating the concentrate and drawing air into it from overhead. Moreover it should be understood that while the oxidant treatment preferably involves directly adding the oxidant to the concentrate, if desired viscous concentrates may be first diluted with an appropriate solvent to facilitate handling prior to said oxidant treatment or with an appropriate triorganophosphorus ligand, e.g., triphenylphosphine, for storage stability prior to said oxidant treatment.

In view of the fact that the oxidant treatment encompassed herein is designed to obtain a desired improvement in the yield of hydridocarbonyltris(triorganophosphorus) rhodium compound over that obtained in the absence of such an oxidant treatment and because the components of the concentrate can vary both in terms of their nature and concentrations, it is apparent that no specific values can be arbitrarily given to conditions such as the amount and partial pressure (concentration) of oxidant, temperature, and contact time for the oxidant treatment. Such conditions which may vary greatly, are not narrowly critical and obviously need only be at least sufficient to obtain the improvement desired. For instance, the amount of oxidant added obviously need only be at least a sufficient amount necessary to achieve an improvement in the yield of hydridocarbonyltris(triorganophosphorus) rhodium compound over that obtained in the absence of such an oxidant treatment. Moreover, there appears to be no upper limit on the maximum amount of oxidant that may be employed save for it obviously not being so great as to create a hazardous explosive situation, e.g. by virtue of large concentrations of oxygen. Thus in some cases a small amount of oxidant may be more beneficial, while in other circumstances a large amount of oxidant may prove more desirable. For example, while only a small amount of oxidant may be needed in a given circumstance, it may be more desirable to use a higher concentration, and therefore a larger amount of oxidant, in order to reduce contact time. Accordingly, treatment conditions such as temperature, partial pressure (concentration) and contact time may also vary greatly depending upon among other things, the oxidant and method of treatment involved, and thus any suitable combination of such conditions may be employed herein. For instance, a decrease in any one of such conditions may be compensated for by an increase in one or both of the other conditions, while the opposite correlation is also true. In general the oxidant may be added to the concentrate at liquid temperatures ranging from 0° C. to about 250° C., while temperatures ranging from about ambient temperature to about 200° C. and more preferably from about 60° C. to about 175° C. should be suitable in most instances. Moreover, oxygen partial pressures ranging from as little as $10^{-4}$ to 10 atmospheres should be sufficient for most purposes, while the organic peroxides can be conveniently added to the concentrate at atmospheric pressure. Of course it is obvious that the contact time will be directly related to such conditions as temperature and oxidant concentration and may vary from a matter of seconds or minutes to hours. For example, very low oxygen partial pressures and a contact time of only a matter of a few seconds may be needed when treating the concentrate with air while it exists as a thin film on the hot walls of an evaporator during the concentration procedure due to the hight temperature employed in such procedures. On the other hand treating a large volume of collected concentrate with moderate oxygen partial pressures ($10^{-3}$ to 1 atmosphere) at room or ambient temperature may require a contact time of several hours or more. In general the preferred oxidative treatment will be at least sufficient to convert any remaining free triorganophosphorus ligand present in the concentrate to its corresponding triorganophosphorus oxide.

Of course it is to be understood that while it is preferred to concentrate the hydroformylation reaction medium via distillation, any suitable concentration procedure or combination of such procedures may be employed if desired. For example, free triorganophosphorus ligand present in the concentrate can also be removed via the use of an alpha,beta unsaturated compound, e.g. maleic acid as taught for example in U.S. Pat. No. 4,283,304, the entire disclosure of which is incorporated herein by reference thereto. In addition, while such is not necessary, if desired, the rhodium complex concentrates employable herein can be washed, both before or after oxygenation, with water, acid or a base compound prior to being employed in the subject invention.

Moreover in general as pointed out above the rhodium complex concentrate employable as the starting material of this invention consists essentially of from about 0.1 to 30 percent by weight of a spent hydroformylation reaction medium having been produced by a process comprising concentrating a spent hydroformylation reaction medium that contains a partially deactivated soluble rhodium hydroformylation catalyst, aldehyde products, higher boiling aldehyde condensation by-products and free triorganophosphorus ligand, so as to remove from said medium, while retaining a major amount of the rhodium of said catalyst present in said medium, at least essentially all, (i.e., at least about 98 percent by weight) and more preferably all of said aldehyde products present in said medium; at least about 50 percent by weight and more preferably at least about 90 percent by weight of said higher boiling aldehyde condensation by-products present in said medium having a boiling point below that of said free triorganophosphorus ligand present in said medium; and at least about 50 percent by weight and more preferably at least about 90 percent by weight of said free triorganophosphorus ligand present in said medium. Of course it is to be further understood that the process of this invention also encompasses the use of starting materials consisting essentially of blends of two or more different rhodium complex concentrates as defined herein. Further the term "essentially non-aqueous" as employed herein in relation to the homogeneous organic reaction solution of the subject process means that said solution may contain a small amount of water, but less than that amount which would destroy the basic integrity of said homogeneous solution by rendering it an aqueous-organic two phase solution. Preferably the only water present in the homogeneous organic reaction solution is that amount which might be normally associated with the possible commercial reactants employable herein and/or which might be formed in situ, e.g. such as when a presolution of alkali metal hydroxide and alcohol is employed.

In general the rhodium complex concentrate employable in this invention may also be considered to consist essentially of rhodium and preferably 0 to about 10 percent by weight of free triorganophosphorus ligand based on the total weight of the concentrate, the remainder of said concentrate consisting essentially of higher boiling aldehyde condensation by-products and phosphorus oxides, said condensation by-products and oxides having generally been produced in situ during the hydroformylation process and/or by said above oxidative treatment of the concentrate. The most preferred rhodium complex concentrate starting materials of this invention are oxygenated rhodium complex concentrates as explained above which are devoid of any said aldehyde products and free triorganophosphorus ligand, any remaining free triorganophosphorus ligand present in the non-oxygenated concentrate having been converted to its corresponding triorganophosphorus oxide by the oxygenation of the concentrate as explained above.

The second main component of the essentially non-aqueous homogeneous organic reaction solution of this invention is hydrogen gas or as the source of hydrogen an alkali metal or alkali earth metal hydroxide, e.g. NaOH, KOH, LiOH, $Mg(OH)_2$, $Ca(OH)_2$, $Ba(OH)_2$, etc., which when employed can react with the alcoholic diluent employed in the process of this invention to furnish the hydrogen radical of the desired hydridocarbonyltris(triorganophosphorus) rhodium product. Thus it is to be understood that if desired one can employ premixtures of such hydroxides and the alcoholic diluent. Of course it is obvious that the amount of hydrogen gas or source of hydrogen need only be employed in an amount sufficient to provide at least that stoichiometric amount of hydrogen necessary to form the desired hydridocarbonyltris(triorganophosphorus) rhodium product, i.e., at least one mole equivalent of hydrogen per mole of rhodium calculated as free metal in the rhodium complex concentrate starting material. In general it is preferred to employ a molar excess of hydrogen. Thus while the upper limit of the amount of hydrogen employed is not critical, it is generally preferred to employ that amount of hydrogen gas or hydrogen source which will provide amounts ranging from about 1 to 500 mole equivalents and more preferably from about 20 to 100 mole equivalents of hydrogen per mole of said rhodium present in the rhodium complex concentrate starting material. Of course it is to be understood that the amount of hydrogen gas or hydrogen source employed should not be so large as to be highly adversely detrimental to the yield of desired hydridocarbonyltris(triorganophosphorus) rhodium product.

While it is preferred to employ hydrogen gas per se as the source of hydrogen, both hydrogen gas and an alkali metal or alkali earth metal hydroxide can be employed in the same individual process if desired for additional beneficial results. For instance it has been found that small amounts of such hydroxides in addition to the use of merely hydrogen gas may also serve to help improve the yield of desired hydridocarbonyltris(triorganophosphorus) rhodium product. In general when employed as such an additional component, amounts of such alkali metal and alkali earth metal hydroxide compounds ranging from about 1 to 50 mole equivalents and more preferably from about 3 to 20 mole equivalents of said hydroxide compounds per mole of rhodium calculated as free metal in the rhodium complex concentrate starting material should be sufficient in most instances.

The third main component of the essentially non-aqueous homogeneous organic reaction solution of this invention is an alcoholic diluent which is employed not only for the purpose of rendering the essential components of the process of this invention miscible with each other and to help maintain the integrity of the novel organic one-phase, homogeneous system of the process of this invention, but as a recovery liquid in which the desired hydridocarbonyltris(triorganophosphorus) rhodium precipitated product is insoluble. While any suitable alcoholic diluent may be employed which would not adversely affect the subject process, it is preferred to employ an alcoholic diluent in which the desired hydridocarbonyltris(triorganophosphorus) rhodium precipitated product is highly insoluble so as to insure recovery of the most optimum yield of desired hydridocontaining rhodium complex possible. Thus in general the preferred alcoholic diluents are aliphatic alcohols containing from 1 to 10 carbon atoms such as methanol, ethanol, propanol, isopropanol, butanol, hexanol, decanol and the like, and more preferably the lower alkanols containing from 1 to 4 carbon atoms. While the amount of alcoholic diluent employed is obviously not critical, when employed amounts ranging from about 50 to about 300 parts by volume of diluent per 100 parts of volume of the rhodium complex concentrate starting material should be sufficient in most instances. More preferably about equal volumes of said organic diluent and said starting material are generally employed. Of course the most preferred amount of organic diluent employable in a given process can be easily determined by simple routine experimentation.

The fourth main component of the essentially non-aqueous homogeneous organic reaction solution of this invention is carbon monoxide gas or a carbon monoxide source. Any suitable carbon monoxide source, as an alternative to carbon monoxide gas per se, may be employed in the present invention which will furnish the carbonyl radical of the desired hydridocarbonyltris(triorganophosphorus) rhodium product. Illustrative sources of carbon monoxide include any organic compound containing an aliphatic carbon to oxygen bond which in the process of this invention will provide the carbonyl radical complexed to the rhodium of the desired product, for example, aldehydes such as formaldehyde, acetaldehyde, benzaldehyde, and the like; amides such as N,N-dimethylformamide, N,N-dimethylacetamide, formanilide, and the like; as well as other such types of compounds providing that they are not adversely detrimental to the purpose of this invention. In general, it is preferred to employ carbon monoxide gas per se. Of course it is obvious that when employed, the source of carbon monoxide need only be employed in an amount sufficient to provide at least that stoichiometric amount of carbon monoxide necessary to form the desired hydridocarbonyltris(triorganophosphorus) rhodium product, i.e., at least one mole equivalent of carbon monoxide per mole of rhodium calculated as free metal in the rhodium complex starting material. The same stoichiometric ratio is of course necessary if one employs carbon monoxide gas per se. In general it is preferred to employ a molar excess of carbon monoxide. Thus while the upper limit of the amount of carbon monoxide employed is not critical, it is generally preferred to employ that amount of carbon monoxide gas or carbon monoxide source which will provide amounts ranging from about 1 to 500 mole equivalents and more preferably from about 20 to 100 mole equivalents of carbon monoxide per mole of said rhodium present in the rhodium complex concentrate starting material. Of course it is to be understood that the amount of carbon monoxide gas or carbon monoxide source employed should not be so large as to be highly adversely detrimental to the yield of desired hydridocarbonyltris(triorganophosphorus) rhodium product.

In general the hydrogen and carbon monoxide gases are normally conveniently employed in the form of a $H_2/CO$ gas mixture. Mole ratios of the gases in such mixtures on the order of from about 20:1 moles of hydrogen to about 1:20 moles of carbon monoxide should be sufficient for most purposes, while the preferred mole ratio of the gases in said $H_2/CO$ mixture is about one to one. Of course it is to be understood that if desired such gaseous mixtures may also contain minor amounts of inert gases such as nitrogen and the like so long as such does not adversely affect the process of this invention.

The fifth main component of the essentially non-aqueous homogeneous organic reaction solution of this invention is a free triorganophosphorus ligand (i.e., ligand that is not complexed with or tied to the rhodium of the partially deactivated rhodium complex catalyst). Any suitable free triorganophosphorus ligand may be employed in the present invention to furnish the triorganophosphorus radicals of the desired hydridocarbonyltris(triorganophosphorus) rhodium complex. Obviously the choice of such phosphorus ligands will merely depend upon the nature of the rhodium complex product desired. Such phosphorus ligands are well known and include those already discussed above. For example in general, the preferred phosphorus ligands are those which have been heretofore employed as rhodium ligands in the hydroformylation field, e.g., as seen by U.S. Pat. No. 3,527,809. Illustrative free triorganophosphorus ligands that may be employed in this invention include, e.g., triorganophosphines, triorganophosphites, triorganophosphinites, triorganophosphonites, and the like, in which the organic radicals are the same or different. Illustrative organic radicals include, e.g., alkyl, aryl, aralkyl, alkaryl and cycloalkyl radicals containing from 1 to 20 carbon atoms, which radicals may further contain groups or substituents, if desired, such as halogen, alkoxy, aryloxy, and the like, which do not essentially interfere with the course of the novel process of this invention. Preferably the triorganophosphorus ligand employed herein is a triorganophosphine, and more preferably a triarylphosphine, especially triphenylphosphine. The amount of free triorganophosphorus ligand employed need only be at least that stoichiometric amount necessary to form the desired hydridocarbonyltris(triorganophosphorus) rhodium product, i.e., at least three mole equivalents of free triorganophosphorus ligand per mole of rhodium calculated as free metal in the rhodium complex concentrate starting material. In general, it is preferred to employ a molar excess of free triorganophosphorus ligand. While the upper limit of the amount of free triorganophosphorus ligand employed is not critical, amounts ranging from about 3 to about 50 mole equivalents, and more preferably from about 4 to about 20 mole equivalents of free triorganophosphorus ligand per mole of said rhodium in the rhodium complex concentrate starting material should be sufficient in most instances. Moreover, it is to be understood that while it is generally preferred to form the homogeneous organic reaction solution employed in this invention with a deliberate charge of said free triorganophosphorus ligand, if the rhodium complex concentrate employed already contains free triorganophosphorus ligand, the amount of such free triorganophosphorus ligand charged may be reduced if desired by that amount already contained in said concentrate. Indeed in some instances if said concentrate contains sufficient free triorganophosphorus ligand it may not even be necessary to employ such a deliberate charge of triorganophosphorus ligand.

As pointed out above the process of this invention comprises reacting at a temperature of from about 20° C. to about 120° C., and more preferably from about 40° C. to about 95° C., an essentially non-aqueous, homogeneous organic reaction solution consisting of (a) a rhodium complex concentrate, (b) hydrogen gas or a hydrogen source, (c) an alcoholic diluent, (d) carbon monoxide gas or a carbon monoxide source and (e) free triorganophosphorus ligand for at least a sufficient period of time to form the desired hydridocarbonyltris(triorganophosphorus) rhodium compound, i.e. $HRh(CO)(PX_3)_3$ wherein $PX_3$ is a triorganophosphorus radical. Formation of the desired hydridocarbonyltris(triorganophosphorus) rhodium product and completion of the reaction can be readily determined and monitored by any suitable conventional method e.g. such as by atomic absorption analysis of aliquot samples of the reaction solution during the process to determine the amount of rhodium calculated as free metal remaining and/or by infrared spectrometry or nuclear magnetic resonance analysis to determine the presence of desired product. Completion of the reaction is evidenced by a constant amount of said rhodium being found in successive aliquot samples of the reaction solution taken to monitor the process. Of course it is to be understood that the particular desired reaction temperature and reaction time with regard to a given process will depend upon such obvious factors as the nature and amounts of the reactive components employed, the amount of product desired, and the like. In general, the reaction process of this invention is preferably conducted at least until a suspension of the desired product is formed in the reaction solution (i.e. mother liquor) as evidenced by the appearance of a precipitate of the desired hydridocarbonyltris(triorganophosphorus) rhodium compound in said solution, and of course most preferably until the reaction is completed, which should normally take several hours.

Moreover the reaction process of this invention may be conducted in any suitable reaction vessel and the reactive organic solution formed merely by combining the essential reactive components of the process in any order desired. In general it is preferred to conduct the process under a gaseous mixture of hydrogen and carbon monoxide. The exact pressure is not critical and any suitable pressure conditions may be employed.

The solid and sparingly soluble complex of hydridocarbonyltris(triorganophosphorus) rhodium precipitate may be isolated and recovered from its product mixture by any suitable method such as by filtration, and the like. The use of a solid bowl centrifuge, such as a Sharples P-600 Super-D-Canter may be useful in increasing the recovery of the precipitate. The recovered wet solids can then be washed, if desired and dried. Of course repeating the subject process of this invention, if desired, using the filtrate or mother liquor of the initial process as the starting material may also increase the total yield of desired product.

The subject process of this invention is indeed unique and provides numerous advantages over heretofore prior art methods. For instance, the subject process involves an organic one-phase reaction, i.e. a reaction that does not require or involve transfer of the rhodium values from one liquid phase to another during the reaction, and thus avoids such disadvantages as handling problems and costly rhodium losses that can accompany prior art liquid phase transfer type process. In addition due to the relatively small volume of organic liquids that would be required in the subject process to convert a given amount of rhodium values to said hydridocarbonyltris(triorganophosphorus) rhodium compounds as compared to the much larger volume of organic liquids and water that would be required by an aqueous phase transfer type process to produce the same amount of desired product from said given amount of rhodium values, it is obvious that the subject invention has the technical advantage over such processes of being able to process such amounts of rhodium values in a much smaller and less expensive reaction vessel, or for equipment of fixed size, to produce more of the desired product in a given period of time. Moreover, the subject process does not possess the environmental and by-product disposal problems that can be attendant with aqueous phase transfer type processes. For example, undesirable by-products of the subject process can easily be disposed of by burning whereas contaminated water must or at least should undergo a water purification treatment before it can be reused or discarded.

More specifically since the subject process of this invention has the distinct advantage of being able to employ starting materials which contain very large amounts of rhodium values and to convert those rhodium values in a simple manner and in a single reaction vessel into high yields of said hydridocarbonyltris(triorganophosphorus) rhodium compounds, the subject process provides an excellent method for recovering the intrinsically deactivated rhodium values of large scale commercial hydroformylation operations as explained above. For reasons not completely understood such deactivated rhodium values are not as easily converted into hydridocarbonyltris(triorganophosphorus) rhodium, as are for example, simple rhodium type monomers and it is believed that the more deactivated such rhodium values are, the more difficult the conversion. However high yields of desired product have been able to be obtained by the subject process of this invention even when the rhodium values are derived from a rhodium complex hydroformylation catalyst that has been employed in a hydroformylation process for a sufficient period of time to become even more than 60 percent deactivated.

The subject process is also considered unique in that it does not require the production of an intermediate halocarbonylbis(triorganophosphorus) rhodium compound and subsequent reduction to the desired hydridocarbonyltris(triorganophosphorus) rhodium compound. Instead the subject process affords a method for preparing hydridocarbonyltris(triorganophosphorus) rhodium directly from the recovered rhodium values of spent rhodium hydroformylation catalysts without necessitating the production of halo-containing rhodium complex intermediates.

The hydridocarbonyltris(triorganophosphorus) rhodium compound products of this invention have a wide range of utility well known in the art, e.g. they are especially suitable for employment in low pressure oxo hydroformylation reactions designed to hydroformylate olefins and produce aldehyde products rich in their normal isomers.

The following examples are illustrative of the present invention and are not to be regarded a limitative. It is to be understood that all of the parts, percentages and proportions referred to herein and the appended claims are by weight unless otherwise indicated, the given amounts of rhodium being calculated as free metal. The symbol $\phi$ in the formulas represents a phenyl radical.

EXAMPLE 1

A spent hydroformylation reaction medium obtained from a continuous hydroformylation process of propylene with carbon monoxide and hydrogen to produce butyraldehyde in the presence of a rhodium complex catalyst consisting essentially of rhodium complex with carbon monoxide and triphenylphosphine, and free triphenylphosphine, said medium containing less than 400 ppm rhodium, and whose catalytic activity had declined to about 30 percent of that of fresh catalyst was concentrated in a thin-film evaporator to remove by distillation, while retaining essentially all of the rhodium of said catalyst, all of the butyraldehyde products present in said medium, more than 90 percent by weight of the aldehyde condensation by-products present in said medium that have a boiling point below that of said free triphenylphosphine ligand present in said medium, and more than 90 percent by weight of said free triorganophosphine ligand present in said medium, and produce a highly viscous rhodium complex concentrate distillation residue consisting essentially of less than about 5 percent by weight of said medium and containing about 11,600 ppm rhodium and a minor amount of free triphenylphosphine ligand (about 2.2 percent by weight based on the total weight of said concentrate), the remainder of said concentrate consisting essentially of higher boiling aldehyde condensation by-products (more than 35 percent by weight of said condensation by-products having a boiling point above that of said free triphenylphosphine ligand) and phosphine oxide.

A solution of about 12.5 grams of said rhodium complex concentrate, about 5.5 grams of triphenylphosphine and 100 ml. of ethanol was prepared and added to a glass pressure bottle which was charged with about 60 psig. of a gaseous mixture of hydrogen and carbon monoxide ($H_2$:CO mole ratio about 1:1) and then vented to one atmosphere. The bottle was similarly flushed with about 60 psig. of said $H_2$:CO mixture. After a final charge of about 60 psig. of the $H_2$:CO mixture, the bottle was set in a 70° C. oil bath for 16.5 hours during which time a greenish yellow suspension of precipitated HRh(CO)(P$\phi_3$)$_3$ was formed. The suspension was filtered and the amount of rhodium recovered as solid HRh(CO)(P$\phi_3$)$_3$ corresponded to a yield of about 28 percent. Infrared spectrometry confirmed that the recovered solid product was indeed hydridocarbonyltris(triphenylphosphine) rhodium as shown by the above formula by exhibiting bands at about 2020 and 1920 cm$^{-1}$ (nujol mull).

EXAMPLE 2

A solution of about 1.33 grams of triphenylphosphine, about 2.84 grams of potassium hydroxide, about 30 ml. of ethanol and about 8.49 grams of a rhodium complex concentrate produced as described in Example 1, said concentrate containing about 14,200 ppm rhodium and a minor amount of free triphenylphosphine ligand (less than about 5 percent by weight based on the total weight of said concentrate), the remainder of said concentrate consisting essentially of higher boiling aldehyde condensation by-products (more than 35 percent by weight of said condensation by-products having a boiling point above that of said free triphenylphosphine ligand) and phosphine oxide, was heated at 95° C. for 1.5 hours. The entire solution was then transferred to a small glass pressure bottle and the bottle pressurized to about 60 psig. with a gaseous mixture of hydrogen and carbon monoxide ($_2$:CO mole ratio about 1:1) and then vented to one atmosphere. The bottle was similarly purged with said $H_2$:CO mixture two more times. The bottle was pressurized with about 60 psig. of the $H_2$:CO mixture a fourth time and then heated at 95° C. for about 3.5 hours during which time a greenish, yellow suspension of precipitated HRh(CO)(P$\phi_3$)$_3$ was formed. The suspension was filtered and the amount rhodium recovered as solid HRh(CO)(P$\phi_3$)$_3$ corresponded to a yield of about 48 percent. Infrared spectrometry confirmed that the recovered solid product was indeed hydridocarbonyltris(triphenylphosphine) rhodium as shown by the above formula by exhibiting bands at about 2020 and 1920 cm$^{-1}$ (nujol mull).

EXAMPLE 3

A solution of about 1.42 grams of triphenylphosphine, a mixture of about 1.52 grams of potassium hydroxide and about 30 ml. of isopropanol, about 0.4 ml. of formaldehyde and about 8.25 grams of a rhodium complex concentrate produced as described in Example 1, said concentrate containing about 9500 ppm rhodium and a minor amount of free triphenylphosphine ligand (less than one percent by weight based on the total weight of said concentrate), the remainder of said concentrate consisting essentially of higher boiling aldehyde condensation by-products (more than 35 percent by weight of said condensation by-products having a boiling point above that of said free triphenylphosphine ligand) and phosphine oxide, was added to a one neck 100 ml. flask. The solution was then heated to 95° C. for 17 hours during which time a greenish, yellow suspension of precipitated HRh(CO)(P$\phi_3$)$_3$ was formed. The suspension was filtered and the amount of rhodium recovered as solid HRh(CO)(P$\phi_3$)$_3$ corresponded to a yield of about 17 percent. Infrared spectrometry confirmed that the recovered solid product was indeed hydridocarbonyltris(triphenylphosphine) rhodium as shown by the above formula by exhibiting bands at about 2020 and 1920 cm$^{-1}$ (nujol mull).

EXAMPLE 4

A rhodium complex concentrate produced as described in Example 1 and containing about 33,300 ppm rhodium and a minor amount of free triphenylphosphine ligand (about 1.8 percent by weight based on the total weight of said concentrate), the remainder of said concentrate consisting essentially of higher boiling aldehyde condensation by-products (more than 35 percent by weight of said condensation by-products having a boiling point above that of said free triphenylphosphine ligand) and phosphine oxide was oxygenated by forming a solution of about 3.56 grams of said concentrate, about 0.58 ml. of tert-butylhydroperoxide and about 10 ml. of ethanol and heating the solution at 60° C. for about 17 hours. Then about 4.52 grams of triphenylphosphine and about 16 ml. of ethanol were added and the solution heated for 19.5 hours at 60° C. under one atmosphere of a gaseous mixture of hydrogen and carbon monoxide ($H_2$:CO mole ratio about 1:1) during which time a greenish, yellow suspension of precipitated $HRh(CO)(P\phi_3)_3$ was formed. The suspension was filtered and the amount of rhodium recovered as solid $HRh(CO)(P\phi_3)_3$ corresponded to a yield of about 60 percent. Infrared spectrometry confirmed that the recovered solid product was indeed hydridocarbonyltris(triphenylphosphine) rhodium as shown by the above formula by exhibiting bands at about 2020 and 1920 cm$^{-1}$ (nujol mull).

EXAMPLE 5

A rhodium complex concentrate produced as described in Example 1 and containing about 27,700 ppm rhodium and a minor amount of free triphenylphosphine ligand (about 5.3 percent by weight based on the total weight of said concentrate), the remainder of said concentrate consisting essentially of higher boiling aldehyde condensation by-products (more than 35 percent by weight of said condensation by-products having a boiling point above that of said free triphenylphosphine ligand) and phosphine oxide was oxygenated by forming a solution of about 4.06 grams of said concentrate, about 1.25 ml. glacial acetic acid, and about 2.2 ml. tertbutylhydroperoxide and heating the solution for about 19 hours at 90° C. Excess acid was recovered by washing the solution with an aqueous 10% NaHCO$_3$ solution; to improve the phase separation about 10 ml. of toluene was then added. The isolated toluene solution was washed with water, and the toluene was then removed in vacuo. To the resulting viscous oxygenated rhodium concentrate liquid were added about 2.87 grams of triphenylphosphine and about 15 ml. of isopropanol. The solution was then heated under a gaseous mixture of hydrogen and carbon monoxide ($H_2$:CO mole ratio about 1:1) at 80° C. for six hours during which time a greenish, yellow suspension of precipitated $HRh(CO)(P\phi_3)_3$ was formed. The suspension was filtered and the amount of rhodium recovered as solid $HRh(CO)(P\phi_3)_3$ corresponded to a yield of about 70 percent. Infrared spectrometry confirmed that the recovered solid product was indeed hydridocarbonyltris(triphenylphosphine) rhodium as shown by the above formula by exhibiting bands at about 2020 and 1920 cm$^{-1}$ (nujol mull).

EXAMPLE 6

A solution of about 1.01 grams of triphenylphosphine, about 25 ml. of ethanol and about 5.31 grams of a rhodium complex concentrate produced as described in Example 1, said concentrate containing about 14,200 ppm rhodium and a minor amount of free triphenylphosphine ligand (less than about 5 percent by weight based on the total weight of said concentrate), the remainder of said concentrate consisting essentially of higher boiling aldehyde condensation by-products (more than 35 percent by weight of said condensation by-products having a boiling point above that of said free triphenylphosphine ligand) and phosphine oxide, was heated at 75° C. under about 60 psig. of a gaseous mixture of hydrogen and carbon monoxide ($H_2$:CO mole ratio about 1:1) for about 16 hours during which time a greenish, yellow suspension of precipitated $HRh(CO)(P\phi_3)_3$ was formed. The suspension was filtered and the amount of rhodium recovered as solid $HRh(CO)(P\phi_3)_3$ corresponded to a yield of about 13 percent. Infrared spectrometry confirmed that the recovered solid product was indeed hydridocarbonyltris(triphenylphosphine) rhodium as shown by the above formula by exhibiting bands at about 2020 and 1920 cm$^{-1}$ (nujol mull).

EXAMPLE 7

About 24 grams of a rhodium complex concentrate produced as described in Example 1 and containing about 9500 ppm rhodium and a minor amount of free triphenylphosphine ligand (less than 1 percent by weight based on the total weight of said concentrate), the remainder of said concentrate consisting essentially of higher boiling aldehyde condensation by-products (more than 35 percent by weight of said condensation by-products having a boiling point above that of said free triphenylphosphine ligand) and phosphine oxide, was oxygenated with air at about 75° C. for about 16 hours (said oxidative treatment being sufficient to convert all free phosphine ligand present in said concentrate to its corresponding phosphine oxide).

A solution of about 8.23 grams of said air treated concentrate, about 1.42 grams of triphenylphosphine, a mixture of about 1.52 grams of potassium hydroxide and about 10 ml. of ethanol, and about 0.4 mol. of 37% formaldehyde was prepared and the solution heated at 80° C. for 16.5 hours during which time a greenish, yellow suspension of precipitated $HRh(CO)(P\phi_3)_3$ was formed. The suspension was filtered and the amount of rhodium recovered as solid $HRh(CO)(P\phi_3)_3$ corresponded to a yield of about 55 percent. Infrared spectrometry confirmed that the recovered solid product was indeed hydridocarbonyltris(triphenylphosphine) rhodium as shown by the above formula by exhibiting bands at about 2020 and 1920 cm$^{-1}$ (nujol mull).

EXAMPLE 8

A rhodium complex concentrate produced as described in Example 1 and containing about 33,300 ppm rhodium and a minor amount of free triphenylphosphine ligand (about 1.8 percent by weight based on the total weight of said concentrate), the remainder of said concentrate consisting essentially of higher boiling aldehyde condensation by-products (more than 35 percent by weight of said condensation by-products having a boiling point above that of said free triphenylphosphine ligand) and phosphine oxide was oxygenated by forming a solution of about 4.93 grams of said concentrate, about 1.5 ml. of glacial acetic acid, and about 2.2 ml. of tert-butylhydroperoxide and heating the solution at 60° C. for 17 hours. After addition of about 20 ml. of toluene, the solution was twice washed with 10% aqueous NaHCO$_3$ and then with water. The toluene was removed in vacuo. To the resulting viscous oxygenated rhodium concentrate liquid were added about 4.21 grams of triphenylphosphine and about 30 ml. of isopropanol. The solution was then heated in a 60° C. oil bath under one atmosphere of a gaseous mixture of hydrogen and carbon monoxide ($H_2$:CO mole ratio about 1:1 for 8 hours during which time a greenish, yellow suspension of precipitated $HRh(CO)(P\phi_3)_3$ was formed. The suspension was filtered and the amount of rhodium recovered as solid HRh(CO)(P$\phi_3$)$_3$ corresponded to a yield of about 75 percent. Infrared spectrometry confirmed that the recovered solid product was indeed hydridocarbonyltris(triphenylphosphine) rhodium as shown by the above formula by exhibiting bands at about 2020 and 1920 cm$^{-1}$ (nujol mull).

EXAMPLE 9

A 0.13 gram sample of the isolated solid HRh(CO)(P$\phi_3$)$_3$ product of Example 1 was diluted with about 2.52 grams of triphenylphosphine and about 47.38 grams of Texanol ® (a mixture of butyraldehyde trimers) and the resulting solution stirred overnight; not all of the solids dissolved. Hence the solution was then set in an 80° C. oil bath for about 10 minutes during which time all but a very small amount of the solids dissolved. The residual solids were removed by filtration to yield a bright yellow solution. The solution was then used to catalyze the hydroformylation of propylene in a stirred autoclave reactor at about 100° C. under about 80 psi. of carbon monoxide, hydrogen and propylene in a 1:1:1 mole ratio. The activity of the rhodium complex catalyst of said process which employed said produced HRhCO(P$\phi_3$)$_3$ solids exhibited a rate propylene hydroformylation of about 1.33 gram-moles per liter per hour. The activity of fresh rhodium complex catalyst using rhodium dicarbonylacetylacetonate as the source of rhodium for said catalyst under the same conditions was about 1.34 gram-moles per liter per hour.

Various modifications and variations of this invention will be obvious to a worker skilled in the art and it is to be understood that such modifications and variations are to be included within the purview of this application and the spirit and scope of the appended claims.

What is claimed is:

1. An organic one-phase process for preparing a hydridocarbonyltris(triorganophosphorus) rhodium compound which comprises reacting, at a temperature of from about 20° C. to about 120° C., an essentially non-aqueous homogeneous organic reaction solution consisting essentially of (a) a rhodium complex concentrate, (b) hydrogen gas or as a source of hydrogen an alkali metal or alkali earth metal hydroxide, (c) an alcoholic diluent containing from 1 to 10 carbon atoms, (d) carbon monoxide gas or a carbon monoxide source and (e) free triorganophosphorus ligand, for at least a sufficient period of time to form said hydridocarbonyltris(triorganophosphorus) rhodium compound; said rhodium complex concentrate consisting essentially of from about 0.1 to about 30 percent by weight of a spent hydroformylation reaction medium and having been produced by concentrating a spent hydroformylation reaction medium that contains a partially deactivated soluble rhodium complex hydroformylation catalyst, aldehyde products, higher boiling aldehyde condensation by-products, and free triorganophosphorus ligand, so as to remove from said medium, while retaining a major amount of the rhodium values of said catalyst present in said medium, at least essentially all of said aldehyde products, at least 50 percent by weight of said higher boiling aldehyde condensation by-products that have a boiling point below that of said free triorganophosphorus ligand present in said medium and at least 50 percent by weight of said free triorganophosphorus ligand present in said medium.

2. A process as defined in claim 1, wherein the rhodium complex concentrate consists essentially of from about 1 to 10 percent by weight of said spent hydroformylation reaction medium.

3. A process as defined in claim 2, wherein said concentrate has been oxygenated, the oxidative treatment being at least sufficient to convert any remaining free triorganophosphorus ligand present in the concentrate to its corresponding triorganophosphorus oxide.

4. A process as defined in claim 3, wherein the oxidative agent is air.

5. A process as defined in claim 3, wherein component (b) is hydrogen gas.

6. A process as defined in claim 5, wherein component (d) is carbon monoxide gas.

7. A process as defined in claim 6, wherein an alkali or alkali earth metal hydroxide is also employed.

8. A process as defined in claim 7, wherein component (c) is an aliphatic alcohol containing from 1 to 4 carbon atoms.

9. A process as defined in claim 4, wherein component (d) is a carbon monoxide source.

10. A process as defined in claim 4, wherein component (e) is triphenylphosphine.

11. A process as defined in claim 4, wherein component (b) is an alkali metal or alkali earth metal hydroxide.

12. A process as defined in claim 4, wherein a suspension of precipitated hydridocarbonyltris(triorganophosphine) rhodium is prepared by heating the essentially non-aqueous, homogeneous reaction solution, at a temperature of from about 40° C. to about 95° C., consisting essentially of (a) said oxygenated rhodium complex concentrate, (b) hydrogen gas, (c) an aliphatic alcohol containing from 1 to 4 carbon atoms, (d) carbon monoxide gas, and (e) free triphenylphosphine ligand.

13. A process as defined in claim 12, wherein the oxidative agent is air.

14. A process as defined in claim 13, wherein an alkali metal or alkali earth metal hydroxide is also employed.

15. A process as defined in claim 14, wherein the hydridocarbonyltris(triphenylphosphine) rhodium compound is isolated and recovered from said suspension.

* * * * *

UNITED STATES PATENT AND TRADEMARK OFFICE
CERTIFICATE OF CORRECTION

PATENT NO. : 4,446,074
DATED : May 1, 1984
INVENTOR(S) : J. D. Jamerson et al.

It is certified that error appears in the above-identified patent and that said Letters Patent is hereby corrected as shown below:

Column 4, line 50, "no" should be ---not---.

Column 6, line 60 "U.S. Pat. No. 4,221,843" should be ---U.S. Pat. No. 4,221,743---.

Column 7, line 25 delete "to about 0.1".

Column 18, line 19 "($_2$:CO" should be ---($H_2$:CO---.

Signed and Sealed this

Thirteenth Day of November 1984

[SEAL]

Attest:

Attesting Officer

GERALD J. MOSSINGHOFF
Commissioner of Patents and Trademarks